United States Patent
Genova et al.

(10) Patent No.: US 6,626,173 B2
(45) Date of Patent: Sep. 30, 2003

(54) DRY POWDER INHALER

(75) Inventors: Perry Genova, Chapel Hill, NC (US); Warren Jewett, Cary, NC (US)

(73) Assignee: IEP Pharmaceutical Devices Inc., Raleigh, NC (US)

( * ) Notice: Subject to any disclaimer, the term of this patent is extended or adjusted under 35 U.S.C. 154(b) by 51 days.

(21) Appl. No.: 09/756,313

(22) Filed: Jan. 8, 2001

(65) Prior Publication Data

US 2002/0088462 A1 Jul. 11, 2002

(51) Int. Cl.[7] .............................................. B65D 83/06
(52) U.S. Cl. ............................ 128/203.15; 128/203.2; 604/58
(58) Field of Search ................. 604/58–64; 128/200.24, 128/203.12–204.16

(56) References Cited

U.S. PATENT DOCUMENTS

| | | |
|---|---|---|
| 5,033,463 A | 7/1991 | Cocozza |
| 5,388,572 A | 2/1995 | Mulhauser et al. |
| 5,460,173 A | 10/1995 | Mulhauser et al. |
| 5,653,227 A | 8/1997 | Barnes et al. |
| 5,694,920 A | 12/1997 | Abrams et al. |
| 5,724,960 A | 3/1998 | Bruna |
| 5,740,793 A | 4/1998 | Hodson et al. |
| 5,918,594 A | 7/1999 | Asking et al. |
| 6,003,512 A | 12/1999 | Gerde |
| 6,006,747 A | 12/1999 | Eisele et al. |
| 6,026,809 A | 2/2000 | Abrams et al. |
| 6,029,662 A | 2/2000 | Marcon |
| 6,237,590 B1 * | 5/2001 | Leedom et al. ......... 128/203.15 |
| 6,378,518 B1 * | 4/2002 | Miekka et al. ......... 128/203.15 |

FOREIGN PATENT DOCUMENTS

| | | |
|---|---|---|
| GB | 1123827 | 8/1965 |
| WO | WO 98/34662 | 8/1998 |
| WO | WO 00/53248 | 9/2000 |

OTHER PUBLICATIONS

International Search Report issued by European Patent Office on corresponding PCT application, mailed Aug. 30, 2002.

* cited by examiner

Primary Examiner—Glenn K. Dawson
(74) Attorney, Agent, or Firm—Frommer Lawrence & Haug, LLP; Ronald R. Santucci

(57) ABSTRACT

A dry powder inhaler having a housing, at least one single dose storage chamber able to contain a single unit dose, a discharge path adjacent the storage chamber, and a flexible and bendable seal plate closing the discharge path. When an air flow under pressure is applied to the top of the dose, the top seal is broken and the dose is driven against the seal plate which deflects away, allowing the powder of the dose to be driven into and along the discharge path. The air flow causes the seal plate (in the discharge path) to vibrate, which acts to break up the dose into particles of preferred size, as the dose is carried along with the air flow and delivered to a patient.

17 Claims, 6 Drawing Sheets

FIG. 2B

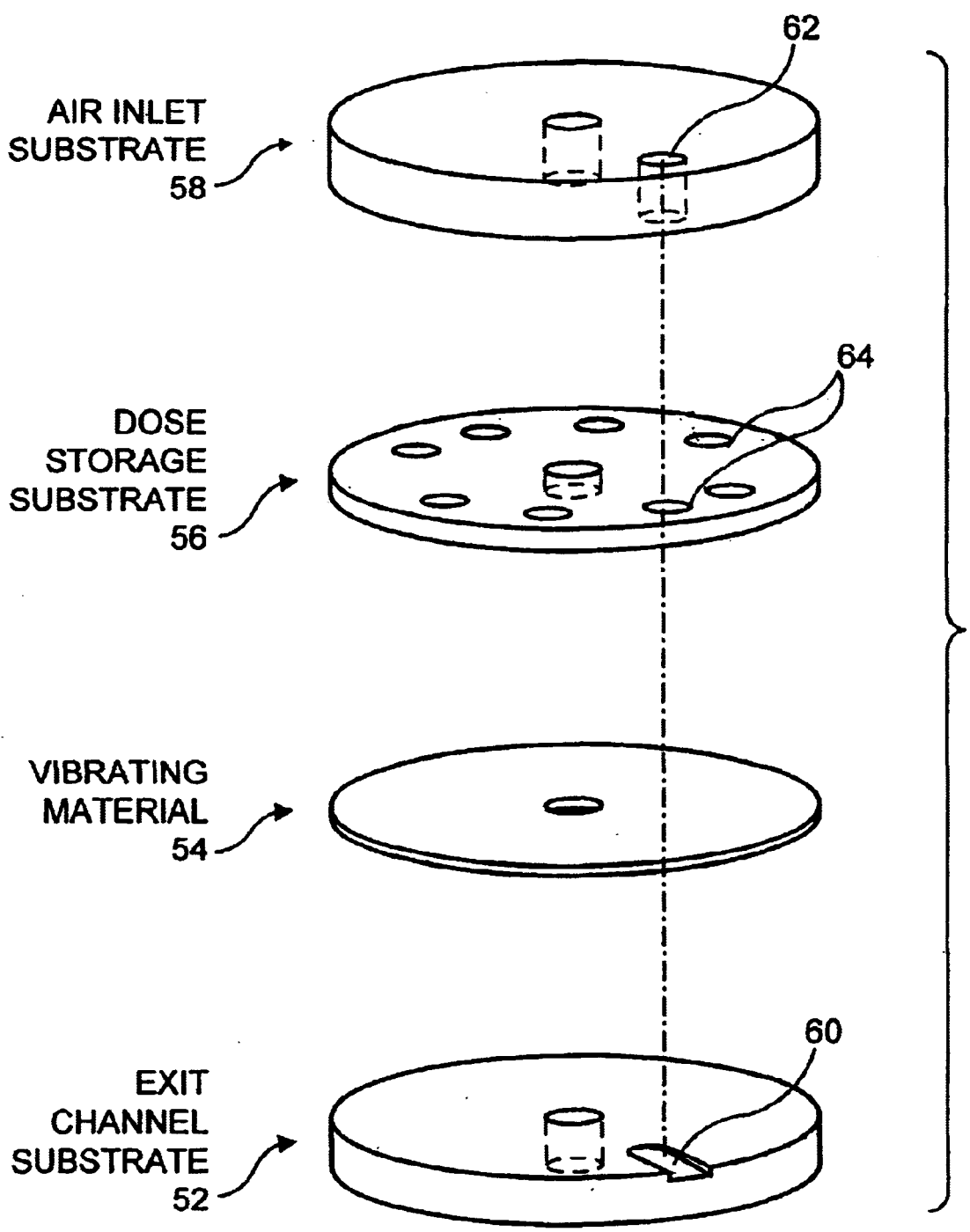
F I G. 6

DRY POWDER INHALER

BACKGROUND OF THE INVENTION

1. Field of the Invention

This invention relates to a medicament inhaler, and more particularly to a dry powder medicament inhaler operable with a source of pressurized air to produce a plume of dry powder particles.

2. Brief Description of the Prior Art

Single unit dose dry powder inhaler devices are known, including some which contain multiple chambers and a selector element for releasing a dose from one chamber at a time. Relevant aspects in the designs of these devices include: establishing the correct dosage size in the device; preserving such dose from humidity and other deleterious environment elements; and delivery of the dose in a preferred particulate size within the discharge air flow.

Stated otherwise, the concerns are charging (filling) the device and storage, release, and delivery of the dose. The stored powder is, by necessity, compacted into a very small volume in an essentially solid state capsule. One of the prominent challenges encountered in design of these systems has been the breakup, or deagglomeration, of the aggregate powder dose into a plume of fine particles which are well disbursed in the air flow. Several such devices have been developed which use a variety of methods to accomplish this end.

U.S. Pat. No. 5,694,920 describes an inhalation device. Powdered medicament is stored in a blister well that is carried in a roll housed in a cartridge. Once the blister well is opened, a vibrator deaggregates the powder in the well and keeps the powder in a fluidized state. An electrostatic plate attracts smaller particles of the powder towards the plate, where they are introduced into an air stream and carried toward a mouthpiece.

U.S. Pat. No. 6,026,809 describes an inhalation device that utilizes vibration to facilitate suspension of a powder in a gas. A piezoelectic vibrator is used to vibrate the powder, thereby deaggregating the powder for optimal suspension in an air stream. A controller is provided for controlling the supply of actuating electricity to the vibrator.

U.S. Pat. No. 5,033,463 describes a multi-dose inhaler for medicaments in powder form. The powder is stored in a container in the inhaler. A certain quantity of powder is withdrawn from the container and conveyed to a dispensing position by a cup. A plunger moves the powder from the cup to a mixing unit. Inhalation causes an impeller in the mixing unit to rotate, thereby mixing air and powder before they enter a user's mouth or nose. Vibrations may be used to facilitate dropping the powder from the container to the cup.

U.S. Pat. No. 6,006,747 describes a dry powder inhaler. The inhaler includes a housing, a cartridge containing medicine supported on the housing, a lid pivotally mounted on the housing, and a mixing chamber. An impeller within the mixing chamber mixes air and the drug before they are inhaled into a patient's lungs.

U.S. Pat. No. 5,918,594 describes an inhaling device capable of breaking down aggregates of powdered medicament to provide particles within the respiratory range. A magazine contains a dose. A deagglomerating device is disposed in the air flow path of the dose. The deagglomerating device is made of opposing surfaces oriented obliquely to a longitudinal direction of the air flow path. When a patient inhales on a mouthpiece, the dose is drawn through the deagglomerating device.

U.S. Pat. No. 6,003,512 describes an apparatus for aerosolizing and dispensing powders. A dose is placed into a chamber for mixing with pressurized air to break up large particles. The dose may be supplied at each administration, or the apparatus may contain a dose reservoir from which individual doses are supplied to the chamber. The dose mixture is moved through an ejecting conduit and into an exit nozzle. The exit nozzle has a sudden increase in diameter to break the pressurized agglomerates into a fine aerosol.

U.S. Pat. No. 6,029,662 describes a compressed air powder inhaler. Powder is stored in a magazine. Powder from the magazine is mixed with compressed air from an air chamber. The powder is fragmented by the flow of air and then by passing through a grille. The release of the compressed air is triggered by a patient sucking on a mouthpiece.

SUMMARY OF THE INVENTION

The present invention is a dry powder inhaler. The inhaler comprises four components: an exit channel, a vibrating means, a dose storage substrate and an air inlet substrate. These four components are stacked together to form the dry powder inhaler. The exit channel is a depression defined in the top surface of the exit channel substrate. The exit channel substrate may have an exit channel per stored dose, or a single exit channel shared by all stored doses. The dose storage substrate has either one, or a plurality of holes, into which a metered dose is stored. From 1 to 350 doses may be individually stored in the dose storage substrate. A vibrating material is placed between the exit channel substrate and the dose storage substrate. An air inlet substrate is positioned above the dose storage substrate. The air inlet substrate may have an air inlet per stored dose, or a single air inlet shared by all the stored doses. A small charge of pressurized air is supplied through the air inlet to the stored dose. The vibrating material deforms due to the air pressure. The powder then exits the inhaler along a trough defined by depression of the vibrating substrate into the exit channel of the exit channel substrate. Air pressure creates a standing wave in the vibrating material that serves to meter the flow of powder from the storage hole, and to deagglomerate and fluidize the stored powder in the air flow.

The present invention overcomes some disadvantages found in prior art inhaler devices, by reducing powder particle size, reducing the occurrence of larger, agglomerated particles, and/or rendering the particles in the flow to be more uniform in size. Furthermore, the present invention accomplishes these ends in an effective, yet simpler and less costly manner when compared to other designs currently available.

BRIEF DESCRIPTION OF THE DRAWINGS

Thus by the present invention its objects and advantages will be realized, the description of which should be taken in conjunction with the drawings wherein:

FIG. 1 is a schematic drawing in perspective view of a simplified embodiment of the new dry powder medicament inhaler.

FIG. 2 is a top planar view of the simplified embodiment of FIG. 1.

FIG. 2A is a sectional view thereof, taken along line 2A–2A' of FIG. 2, showing the inhaler before activation.

FIG. 2B is similar to FIG. 2A, but shows the inhaler during activation.

FIG. 2C is a front elevation view of FIG. 1 before activation.

FIG. 2D is similar to FIG. 2C, but shows the inhaler during activation.

FIG. 6 is a schematic drawing, in perspective, showing an exploded view of a third embodiment of the new inhaler.

DETAILED DESCRIPTION OF THE PREFERRED EMBODIMENTS

Figure 1:
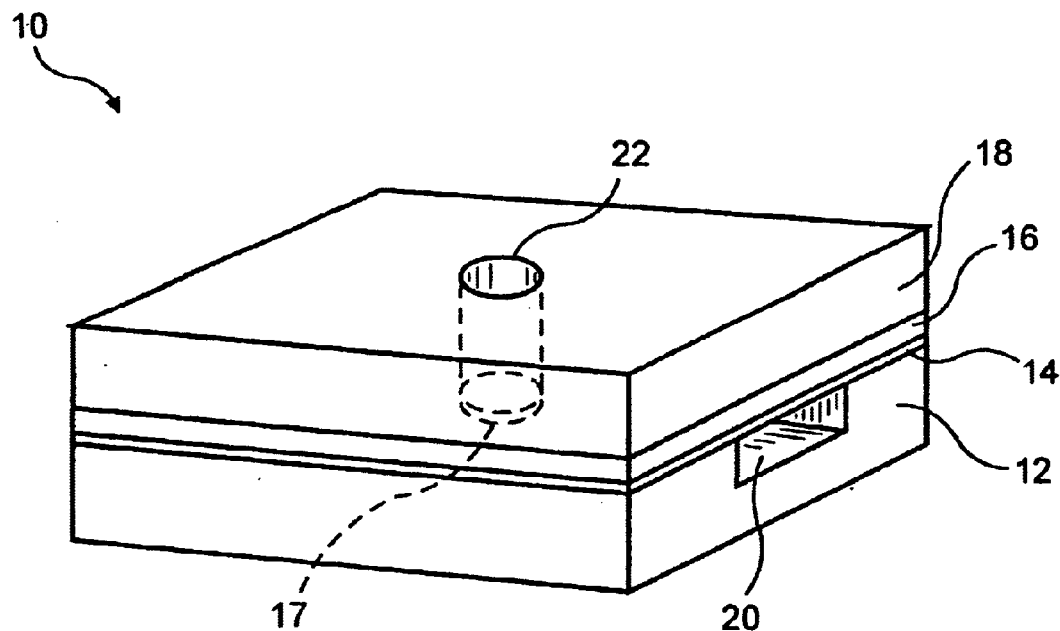
Figure 2:
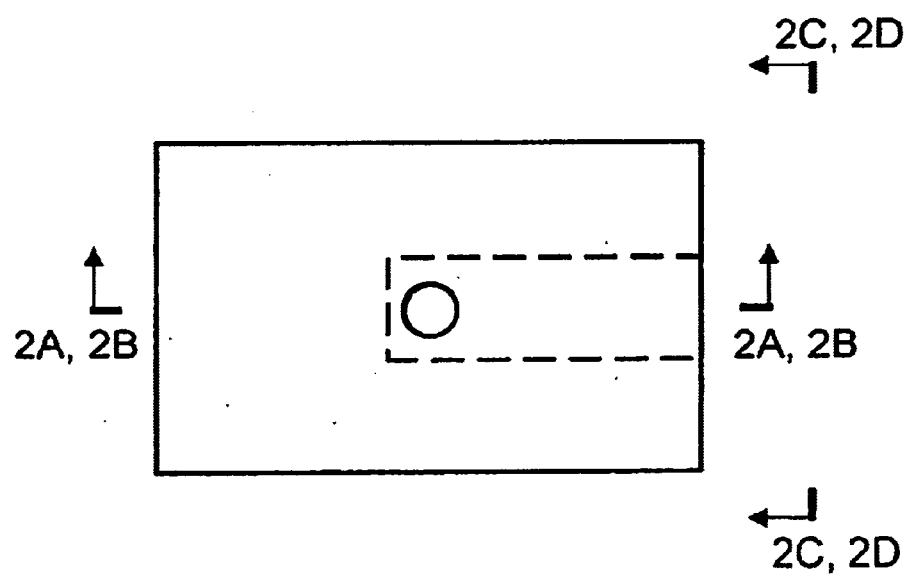
Figure 2A:
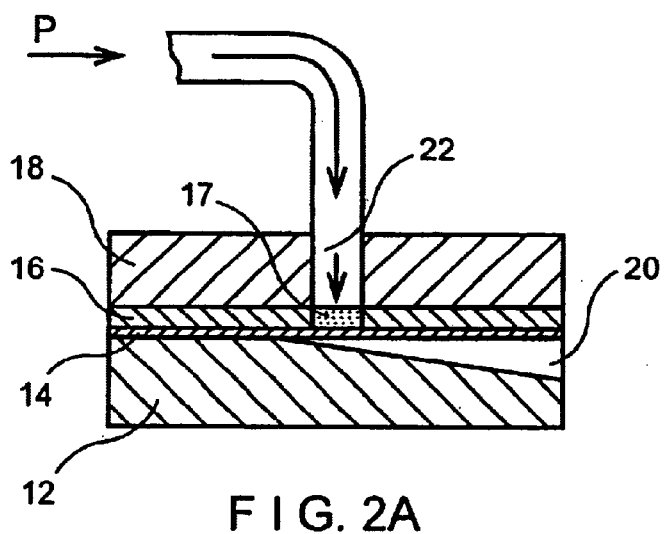
Figure 2B:
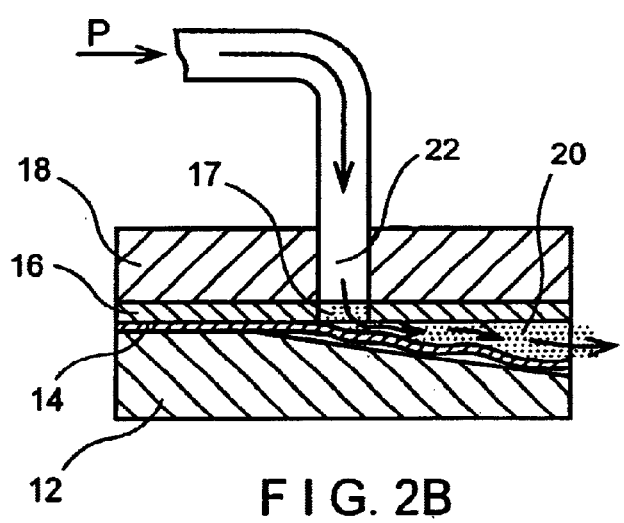
Figure 2C:
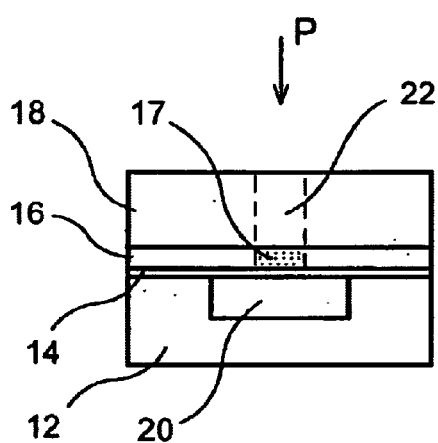
Figure 2D:
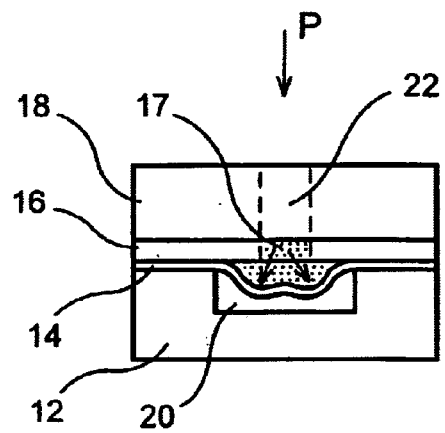
Figure 3:
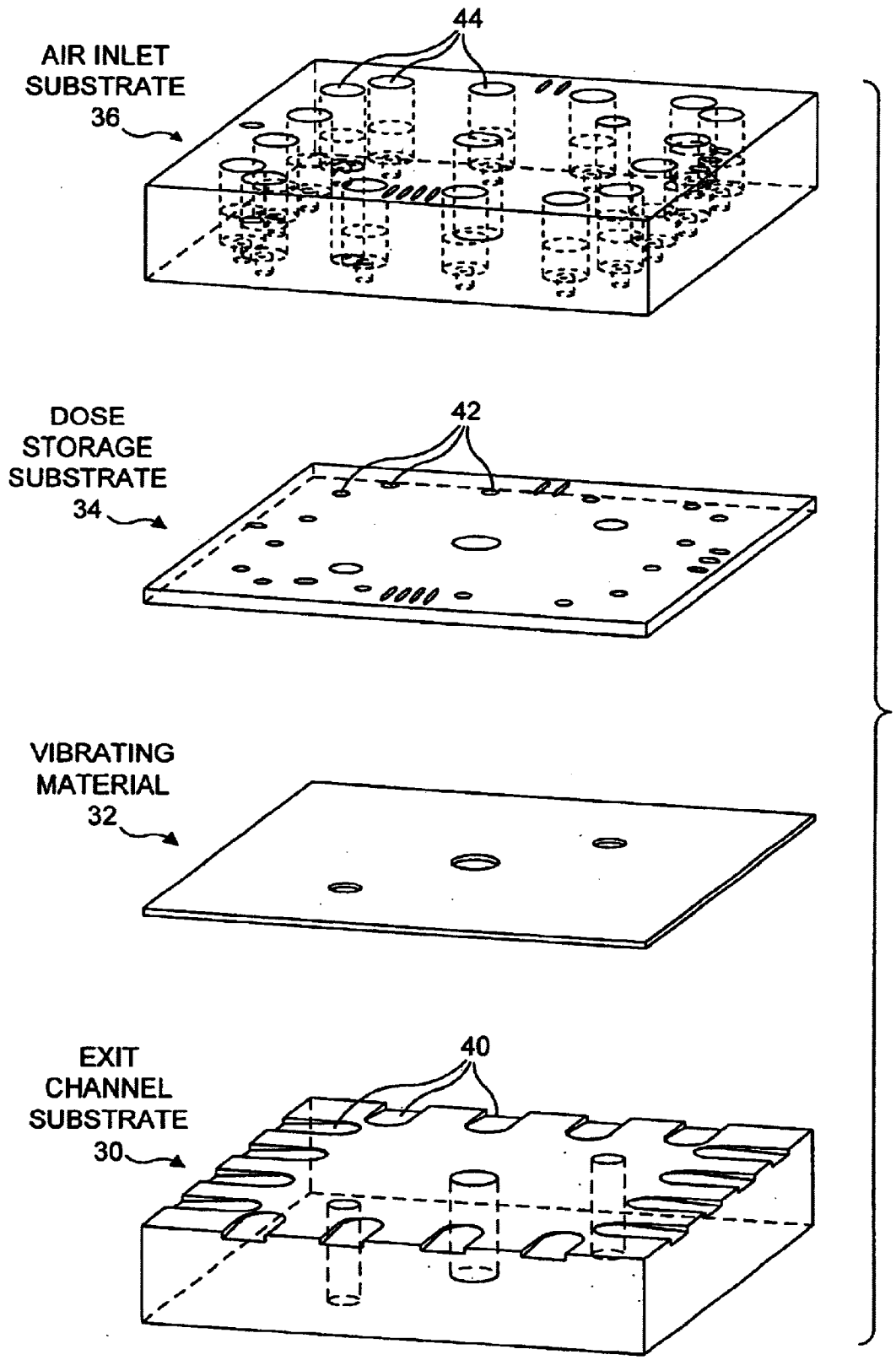
FIG. 3 is a schematic drawing, in perspective, showing an exploded view of a second embodiment of the new inhaler.
Figure 4:
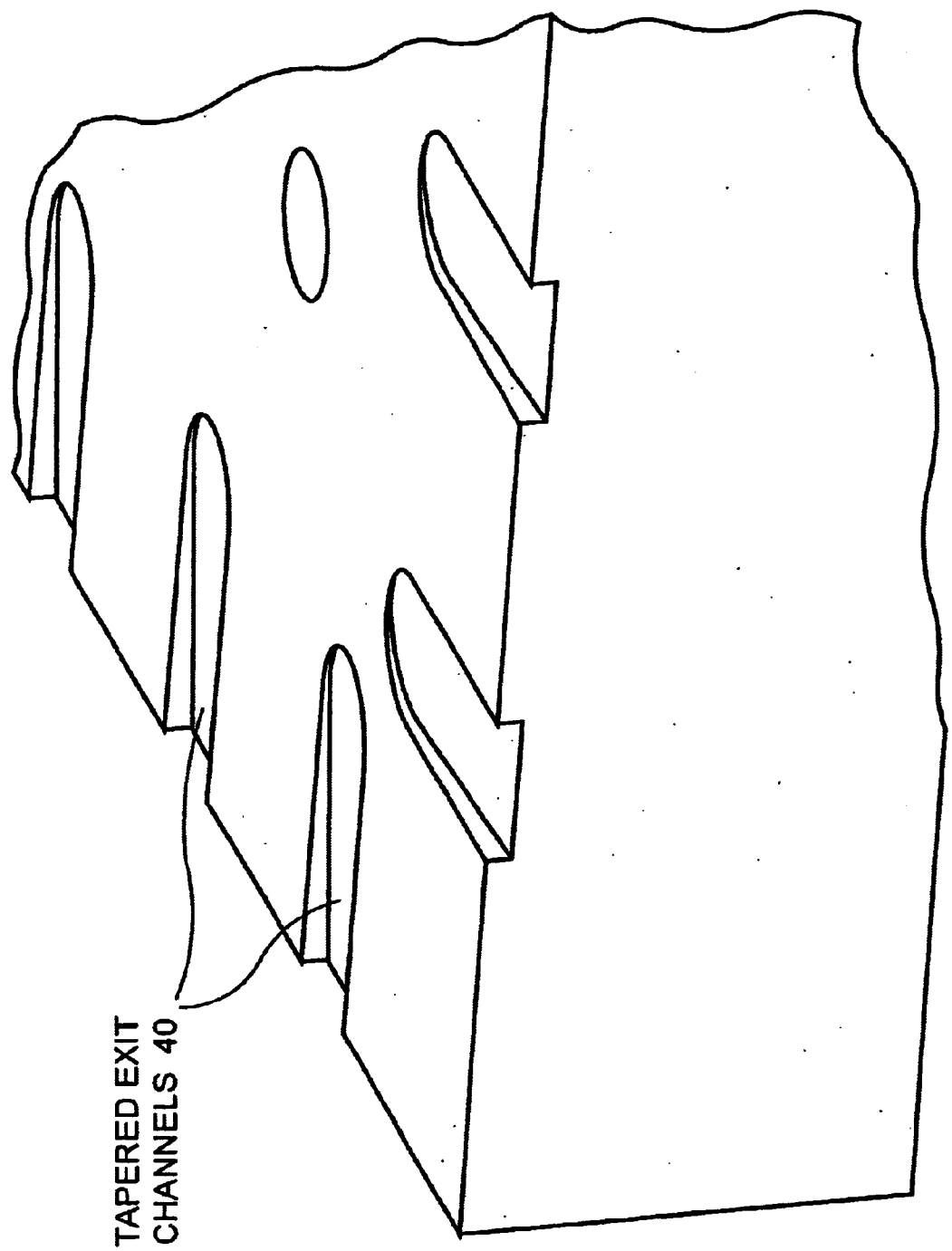
FIG. 4 is a fragmentary and enlarged view of the exit channel substrate of FIG. 3.
Figure 5:
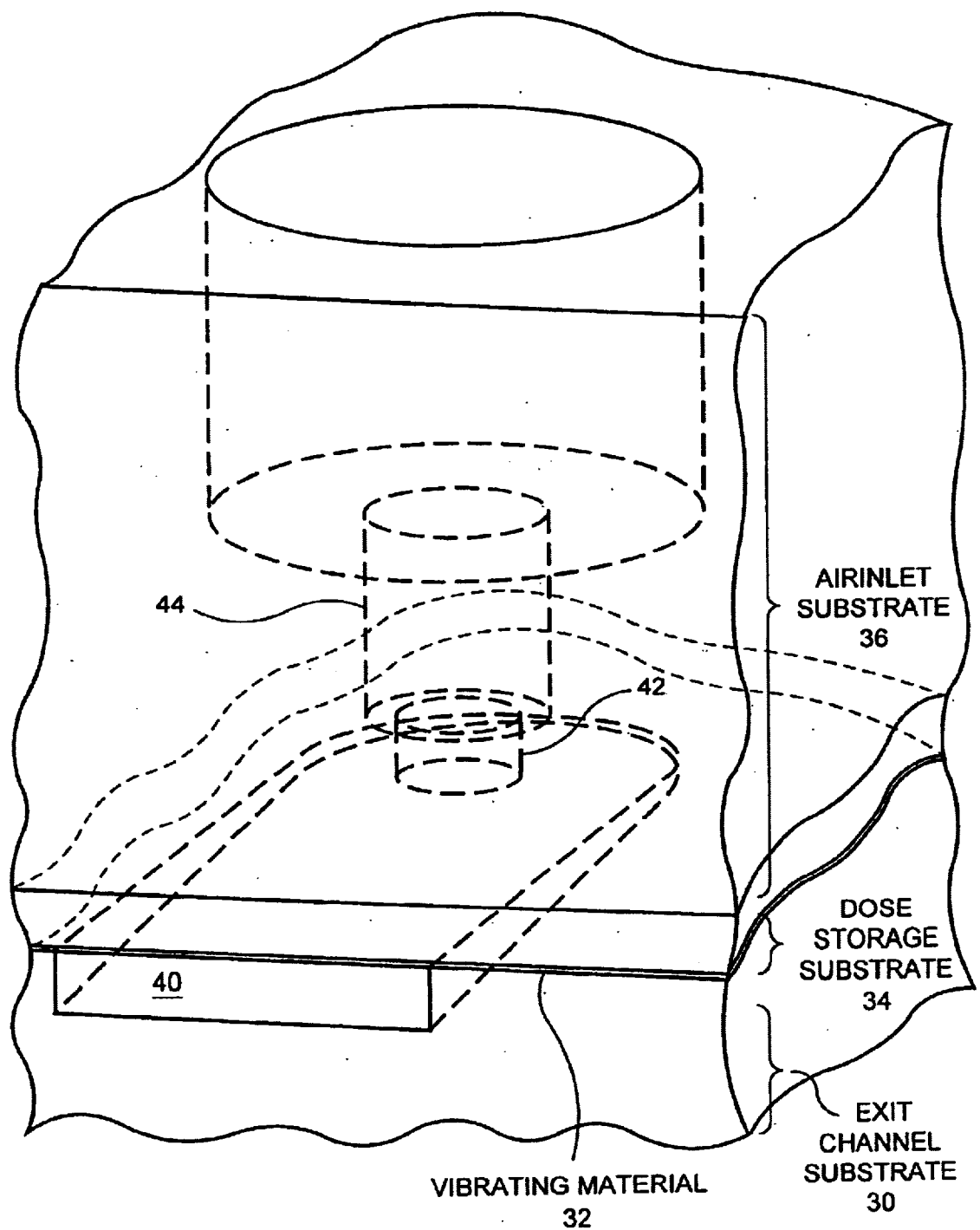
FIG. 5 is a schematic perspective view of the inhaler of FIG. 3, showing the alignment of the exit channel, dose storage chamber and air inlet channel.

Dose storage and deagglomeration are critical elements of unit dose dry powder inhaler devices. Combining the storage and deagglomeration elements into a single component, which accommodates both functions is desirable from a device engineering perspective, provided the powder is well protected from ambient conditions—particularly humidity—and achieves performance targets for drug delivery through the device. Metering of a dry powder can be most accurately and cost effectively achieved in a factory setting. The dry powder is metered in a factory environment directly into the storage/deagglomeration device described here. This device, when combined with supplemental energy such as pressurized air, produces a plume of dry powder with particle sizes in the respirable range. The invention includes four basic components, namely, a bottom substrate defining therein an exit channel, above that a sheet of vibrating material, above that a dose storage substrate, and above that an air inlet substrate.

Turning now more particularly to the drawings, FIG. 1 shows schematically a simplified embodiment 10, of the new inhaler, comprising the bottom or exit channel substrate 12, the vibrating sheet substrate 14, the dose storage substrate 16, and the air inlet substrate 18. At the front is an exit discharge opening 20, and at the top is an inlet opening 22, for pressurized air. The exit channel substrate, dose storage substrate and air inlet substrate may be fabricated from any material suitable for that purpose, including a metal such as aluminum, or a plastic, such as ABS, polypropylene, polyethylene, etc.

The exit channel substrate is a base including at least one sloped exit channel, which is tapered so that it is shallow at its beginning or inlet and deeper at its exit opening. In the preferred embodiment, the channel is situated in a top surface of this base or exit channel substrate, the channel defining a grooved passageway in the solid substrate and being open at the top. The walls of the exit channel in the preferred embodiment are parallel in their vertical dimension. The top of the open channel or groove defines a top plane.

FIGS. 2A through 2D illustrate the use and effect of the sheet of vibrating material. The single unit dose is an agglomerated pellet of medicament powder situated in storage chamber 17, situated in the dose storage substrate 16. The unit dose is protected within the storage chamber by a protective seal. Pressurized air is supplied from a source (not shown) which provides pressurized air in the range of 1 to 60 psi., and a burst of pressurized air is applied to the dose for a period of 10 to 1000 milliseconds.

The pressurized air travels along a passage 22, in the air inlet substrate 18, to impact on and break open the seal containing the single unit dose of drug, and blow the solid dose out through the exit passage 20, in the exit channel substrate 12. Below the dose storage substrate 16, is a vibrating sheet substrate 14, which may be made preferably of 0.0005 to 0.020 in. thick Mylar film or other material appropriately sized and suitable for that purpose. This film is flexible and stretchable. When the blast of pressurized air blows the aggregate's powder downward against the vibrating sheet, the sheet deflects downward into the channel as seen in FIGS. 2B and 2D, allowing the air and powder mixture to flow through and out of the exit channel. As the flow of air and powder passes over the vibrating sheet, the sheet is induced to vibrate in a whipping or flopping motion as generally indicated in FIGS. 2B and 2D at a frequency of 10 to 60 KHz. This whipping motion of the vibrating sheet effectively breaks the powder carried by the air flow into smaller and more uniform particles, thus deagglomerating the solid into a fine powder. The particle size achieved is in the range of 2 to 8 microns, which is in the respirable range. Also, the air flow over the Mylar sheet creates a standing wave that has the effect of metering the dose into the air stream.

FIG. 3 is an exploded perspective view of a second embodiment of the invention, which is essentially the same in concept as the embodiment of FIG. 1, however, the dose storage substrate 34, has sixteen single unit dose storage chambers instead of one. Also, the exit channel substrate 30, has sixteen separate exit channels, one for each dose. In this embodiment the air supply (not shown) is rotatably situated above the air inlet substrate 36. The air supply would be rotated relative to the aligned air inlet 44, dose storage chamber 42 and exit channel 40.

FIG. 4 shows the exit channel substrate 30, of FIG. 3. The exit channel 40, is shown to be tapered downward as the air flow moves outward from the area below where a unit dose is stored to the exit opening. In addition, the side walls of the channel are vertical and parallel in relation to the flow direction of the channel. However, other embodiments are possible, such as a flat air flow channel, or a channel which has a tapered width in the direction of air flow, or side walls which are tapered or rounded.

FIG. 5 shows the alignment of the four elements of FIG. 3 with the air inlet 44, positioned directly above the dose storage chamber 42, which in turn is positioned directly over the exit channel 40. The vibrating sheet is between the dose storage and air exit channel.

FIG. 6 shows an exploded view of another preferred embodiment, that of a round, multi-dose device which has one exit channel 60, defined in the exit channel substrate 52, and one air inlet passageway 62, defined in the air inlet substrate 58. The dose storage substrate 56, has a plurality of dose storage chambers 64, defined therein. The dose storage substrate is positioned between the vibrating sheet 52, and the air inlet substrate 58. The air inlet passageway 62, is fixed in orientation over the exit channel 60. The individual dose chambers 64, are positioned in the line of the air inlet and exit channel by rotating the dose storage substrate.

Thus by the present invention its objects and advantages are realized and although preferred embodiments have been disclosed and described in detail herein, its scope should not be limited thereby rather its scope should be determined by that of the appended claims.

We claim:

1. A dry powder inhaler operable with a source of pressurized air, comprising:

a—a base substrate having top and front surfaces with an exit channel in the form of a trough defined in said top surface and extending lengthwise to and intersecting said front surface;

b—a sheet of flexible material overlying said top surface of said base substrate;

c—a dose storage substrate overlying said sheet, said dose storage substrate containing at least one single unit dose of agglomerated medicament powder, said dose storage substrate having a bottom surface adjacent said sheet, at least one chamber defined therein to contain said unit dose, and an opposite top surface, d—an air inlet substrate overlying said dose storage substrate and including at least one passageway for directing pressurized air from a source onto said top surface of said dose storage substrate, said pressurized air forcing said dose from said chamber, said sheet being deformed by said pressurized air downward into said trough, thus providing a discharge passage along said top surface of said sheet, and said dose being driven downward by application of said pressurized air, and forced against said sheet, said sheet vibrating so as to deagglomerate and fluidize said dose and meter the flow of powder through said trough, said dose being carried in a fluidized form through said trough, and said dose exiting from said front surface of said base substrate.

2. An inhaler according to claim 1 wherein said pressurized air is applied at a pressure in the range of 1–100 psi.

3. An inhaler according to claim 2 wherein said pressurized air is applied to said dose for a duration in the range of 10-milliseconds to 1000-milliseconds.

4. An inhaler according to claim 1 wherein said pressurized air is applied to said dose for a duration in the range of 10-milliseconds to 1000-milliseconds.

5. An inhaler according to claim 1 wherein a standing wave in said vibrating sheet operates in a frequency range of 10–60 kHz.

6. An inhaler according to claim 1 wherein said sheet comprises a Mylar film having thickness in the range of 0.0005 to 0.020 inches.

7. An inhaler according to claim 1 which produces a discharge in the form of a plume of dry powder particles sized in the range of 2–8 microns.

8. An inhaler according to claim 1 wherein said unit dose is protected by a protective seal, which is broken upon activation of said pressurized air source.

9. An inhaler according to claim 1 wherein said trough has inlet and exit ends, and said trough is sloped so that it becomes deeper in the direction of its exit end.

10. An inhaler according to claim 9 wherein said trough has generally parallel side walls.

11. An inhaler according to claim 1 wherein:

a said base substrate has a plurality of said troughs spaced apart from each other, b said sheet overlies all of said troughs, c said dose storage substrate contains a plurality of single unit doses, each of said unit doses being situated within chambers defined in said dose storage substrate, each of said chambers being situated so as to align with and overlie one of said troughs, and d said air inlet substrate having at least one passageway laterally movable to overlie and be directed selectively to each of said stored single unit doses, said pressurized air being applicable via said air inlet substrate selectively to each of said doses to be directed as a plume of powder from its respective exit channel.

12. An inhaler according to claim 1 wherein:

a said base has a single exit channel, b said sheet overlies said trough, c said air inlet substrate has at least one passageway, said passageway being fixed in a position over said trough, d said dose storage substrate contains a plurality of single unit doses, said dose storage substrate capable of being rotatably positioned and aligned over said trough and beneath said air inlet passageway, said pressurized air being applicable via said passageway selectively to each of said doses to be directed as a plume of powder from said trough.

13. A method of deagglomerizing a dose of agglomerated dry powder in an inhaler where pressurized air is applied to said dose, blowing it through an exit channel having inlet and exit ends, comprising the steps:

a providing a sheet of vibratable material in said exit channel, extending generally from said inlet to said exit end, b directing said pressurized air carrying said dry powder to flow along the surface of said sheet in said exit channel thereby causing said sheet to stretch deform and vibrate and create a standing wave in said sheet, whereby said standing wave helps to deagglomerize and fluidize said powder in said pressurized air flow.

14. A method according to claim 13 wherein said pressurized air is applied at a pressure in the range of 1–100 psi.

15. A method according to claim 13 wherein said pressurized air is applied for a duration in the range of 10-milliseconds to 1000-milliseconds.

16. A method according to claim 13 wherein said vibrating sheet operates in a frequency range of 10–60 kHz.

17. A method according to claim 13 wherein said deagglomerated dry powder has particles sized in the range of 2–8 microns.

* * * * *